(12) United States Patent
Davis

(10) Patent No.: US 9,533,062 B2
(45) Date of Patent: Jan. 3, 2017

(54) AUTOMATIC TONOMETER TIP DISINFECTION APPARATUS

(71) Applicant: Andrew Peter Davis, Bellevue, WA (US)

(72) Inventor: Andrew Peter Davis, Bellevue, WA (US)

( * ) Notice: Subject to any disclaimer, the term of this patent is extended or adjusted under 35 U.S.C. 154(b) by 162 days.

(21) Appl. No.: 14/550,738

(22) Filed: Nov. 21, 2014

(65) Prior Publication Data

US 2015/0144163 A1    May 28, 2015

Related U.S. Application Data

(62) Division of application No. 13/187,389, filed on Jul. 20, 2011, now abandoned.

(60) Provisional application No. 61/399,900, filed on Jul. 20, 2010, provisional application No. 61/516,090, filed on Mar. 28, 2011.

(51) Int. Cl.
*A61L 2/18* (2006.01)
*A61L 2/24* (2006.01)

(52) U.S. Cl.
CPC .. *A61L 2/18* (2013.01); *A61L 2/24* (2013.01); *A61L 2202/17* (2013.01); *A61L 2202/24* (2013.01)

(58) Field of Classification Search
CPC ................ A61L 2/16; A61L 2/18; A61L 2/24; A61L 2202/17; A61L 2202/24
See application file for complete search history.

(56) References Cited

U.S. PATENT DOCUMENTS

| | | | | | |
|---|---|---|---|---|---|
| 2,615,455 | A | * | 10/1952 | Persson | 134/58 R |
| 2,886,046 | A | * | 5/1959 | Du Gal | 134/58 R |
| 4,381,285 | A | * | 4/1983 | Wittenberg | 422/116 |
| 4,735,209 | A | * | 4/1988 | Foody | 600/406 |
| 4,816,232 | A | * | 3/1989 | Barrau et al. | 422/301 |
| 4,922,914 | A | * | 5/1990 | Segal et al. | 600/406 |
| 5,053,207 | A | * | 10/1991 | Lervick | 422/300 |
| D340,530 | S | * | 10/1993 | Conrad | D24/217 |
| 5,318,030 | A | * | 6/1994 | Williams | 600/406 |
| 5,628,971 | A | * | 5/1997 | Norman | 422/301 |
| 6,508,257 | B1 | * | 1/2003 | Rich | 134/25.3 |

* cited by examiner

*Primary Examiner* — Regina M Yoo
(74) *Attorney, Agent, or Firm* — Lowe Graham Jones PLLC

(57) ABSTRACT

A tonometer tip disinfection apparatus for disinfecting and rinsing a tonometer tip includes a first basin configured to hold a disinfecting solution, a second basin configured to hold a rinsing solution, a holding platform configured to receive at least one tonometer tip, a tonometer tip support arm configured to support a tonometer tip having a tip end in an orientation allowing the tip end to reside at least in part within the first and second basins, and a transportation assembly configured to automatically move the tonometer tip support arm between the first and second basins and the holding platform.

10 Claims, 5 Drawing Sheets

9,533,062 B2

AUTOMATIC TONOMETER TIP DISINFECTION APPARATUS

PRIORITY CLAIM

This application is a division of U.S. application Ser. No. 13/187,389, filed Jul. 20, 2011, which claims the benefit of U.S. Provisional Application No. 61/399,900 filed on Jul. 20, 2010, and U.S. Provisional Application No. 61/516,090 filed on Mar. 28, 2011, the subject matter of which are incorporated herein by reference.

FIELD OF THE INVENTION

This invention relates generally to eye-testing machines and apparatus and, more specifically, to an automatic tonometer tip disinfection apparatus.

BACKGROUND OF THE INVENTION

One of the most common tools used in an eye exam is the Goldmann Applanation Tonometer, which measures the eye pressure when a small plastic tip is gently placed against the anesthetized cornea. This small plastic tip must be disinfected between patients. The current recommended method is to leave the tip in 3% peroxide for 5 to 10 minutes, followed by rinsing in water. If, however, the plastic tip is left too long in the peroxide, corrosion will occur to the plastic and require it to be replaced at substantial cost and inconvenience. In a busy office with multiple tonometers, multiple patients and multiple staff, losing track of how long the tonometer tip has been in the peroxide, or leaving the tips in the peroxide overnight, is a frequent occurrence. In addition, it is possible with this regimen that a small amount of disinfectant could remain on the tip, or that some disinfectant could accumulate in the water bath after several uses of a disinfecting solution. Accordingly, there is need for an automatic apparatus to soak the tip in peroxide for a predetermined period of time and thereafter remove the tip from the peroxide, rinse it with water one or more period of time, and dry it out.

SUMMARY OF THE INVENTION

In one aspect of the present invention, a tonometer tip disinfection apparatus for disinfecting and rinsing a tonometer tip includes a first basin configured to hold a disinfecting solution, a second basin configured to hold a rinsing solution, a holding platform configured to receive at least one tonometer tip, a tonometer tip support arm configured to support a tonometer tip having a tip end in an orientation allowing the tip end to reside at least in part within the first and second basins, and a transportation assembly configured to automatically move the tonometer tip support arm between the first and second basins and the holding platform. In alternative embodiments, the apparatus may include a support base to which the first basin, second basin and holding platform are attached.

In another aspect of the present invention, an automatic tonometer tip disinfection apparatus for disinfecting and rinsing a tonometer tip includes a support base, a first basin attached to the support base and configured to hold a disinfecting solution, at least one additional basin attached to the support base and configured to hold a rinsing solution, a tonometer tip support arm configured to support a tonometer tip having a tip end in an orientation allowing the tip end to reside at least in part within the first and at least one additional basins, and a transportation assembly configured to automatically move the tonometer tip support arm between the first and at least one additional basins.

In alternative embodiments, the basins may be adjacent each other and may have fluid level marks indicating the preferred level of fluid to be supplied to each basin. The tonometer tip support arm may be pivotally connected to the transportation assembly and include a counterweight that orients the holding ring to allow the tip end to reside at least in part within the basins. The tonometer tip support arm may also be configured for vertical movement to allow the tonometer tip end to be lowered into each basin and raised for movement between basins. The transportation assembly may move the tonometer tip support arm from basin to basin according to a predetermined time function. The transportation assembly may include a mechanical rotating timer that rotates according to a predetermined time function, an electronic timing circuit and rotating gear that rotates according to a predetermined time function, a motorized track that moves according to a predetermined time function, or the like. The embodiments may further include additional basins configured to hold additional rinsing solution.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

Figure 1:
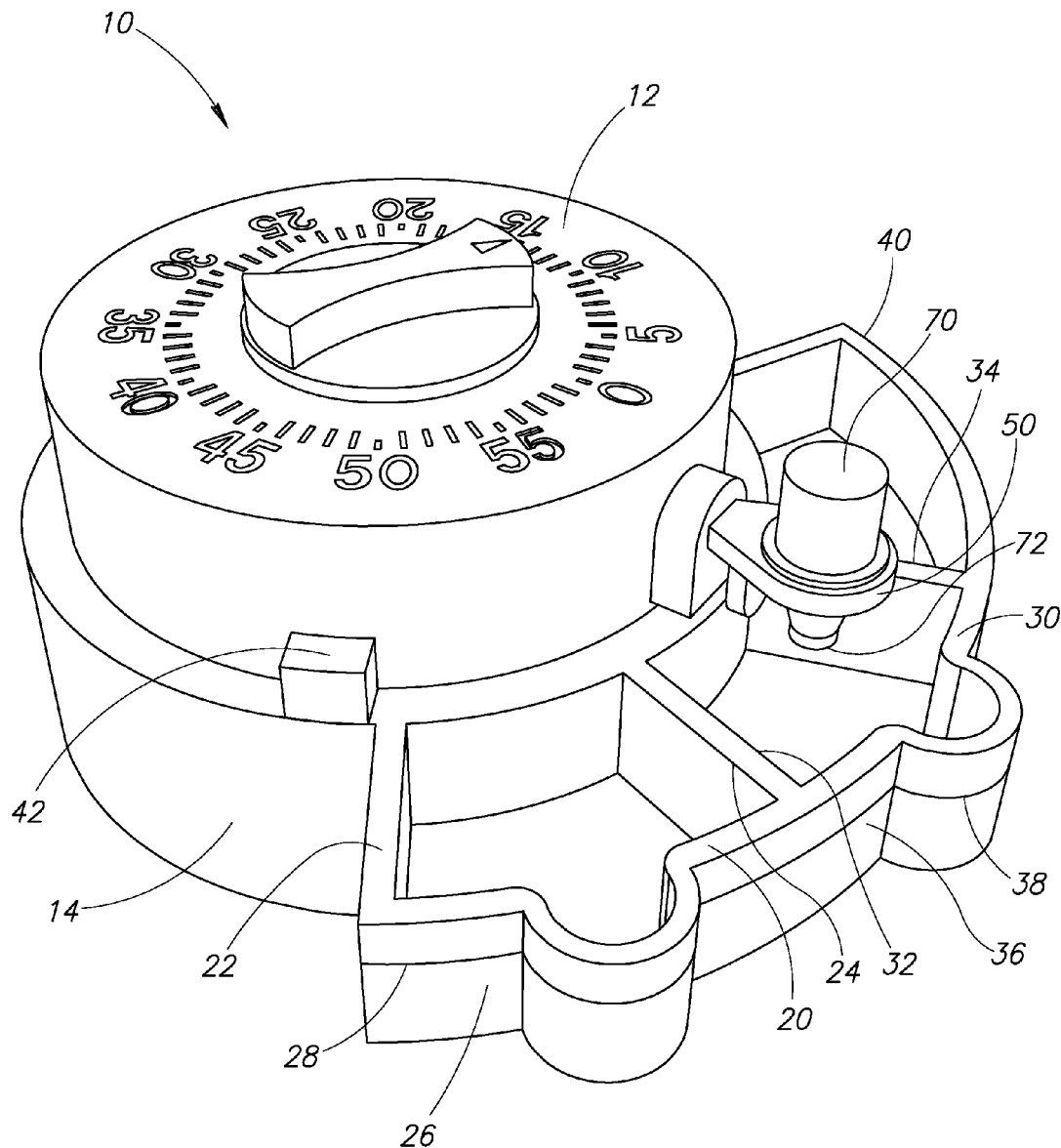
FIG. 1 is a perspective view of an automatic tonometer tip disinfection apparatus according to an embodiment of the present invention.

Referring to FIG. 1, the apparatus 10 includes a mechanical rotating timer 12 preferably mounted to a supportive base 14, for example, made of a plastic or like material. The base 14 supports or is otherwise affixed to or associated with a first basin 20 having a front wall 22, a back wall 24, and a side wall 26 preferably including a fluid level mark 28, which basin holds a disinfecting solution, for example, peroxide. In one embodiment, the fluid level of the rinsing solution is set to be higher than the fluid level of the disinfecting solution in order to ensure that the disinfecting solution is completely removed from the tonometer tip. The base 14 supports or is otherwise affixed to or associated with a second basin 30 having a front wall 32 preferably adjacent to or coextensively formed with the back wall 24 of the first basin 20, a preferably raised back wall 34, and a side wall 36 preferably including a fluid level mark 38, which basin holds a rinsing solution, for example, water. A holding platform 40 affixed to or associated with the base is preferably positioned adjacent the back wall 34 of the second basin 30. The basins 20,30 and holding platform 40 are preferably circumferentially positioned around the timer 12 in sequence from the first basin 20 to the second basin 30 and ending with the holding platform 40. Fluid level marks 28,38 provide ready indication of the preferred level of fluid to be supplied to each basin. A tonometer holding assembly 50 is affixed or otherwise securely mounted to the side of the rotating timer 12 and provides preferably friction fit support for a tonometer tip 70 having a tip end 72 to be disinfected. A bumper 42, preferably made of a substantially rigid but resilient material such as plastic or rubber or the like is attached to the rim of the base 14 preferably near the front wall 22 of the first basin 20.

Figure 2:
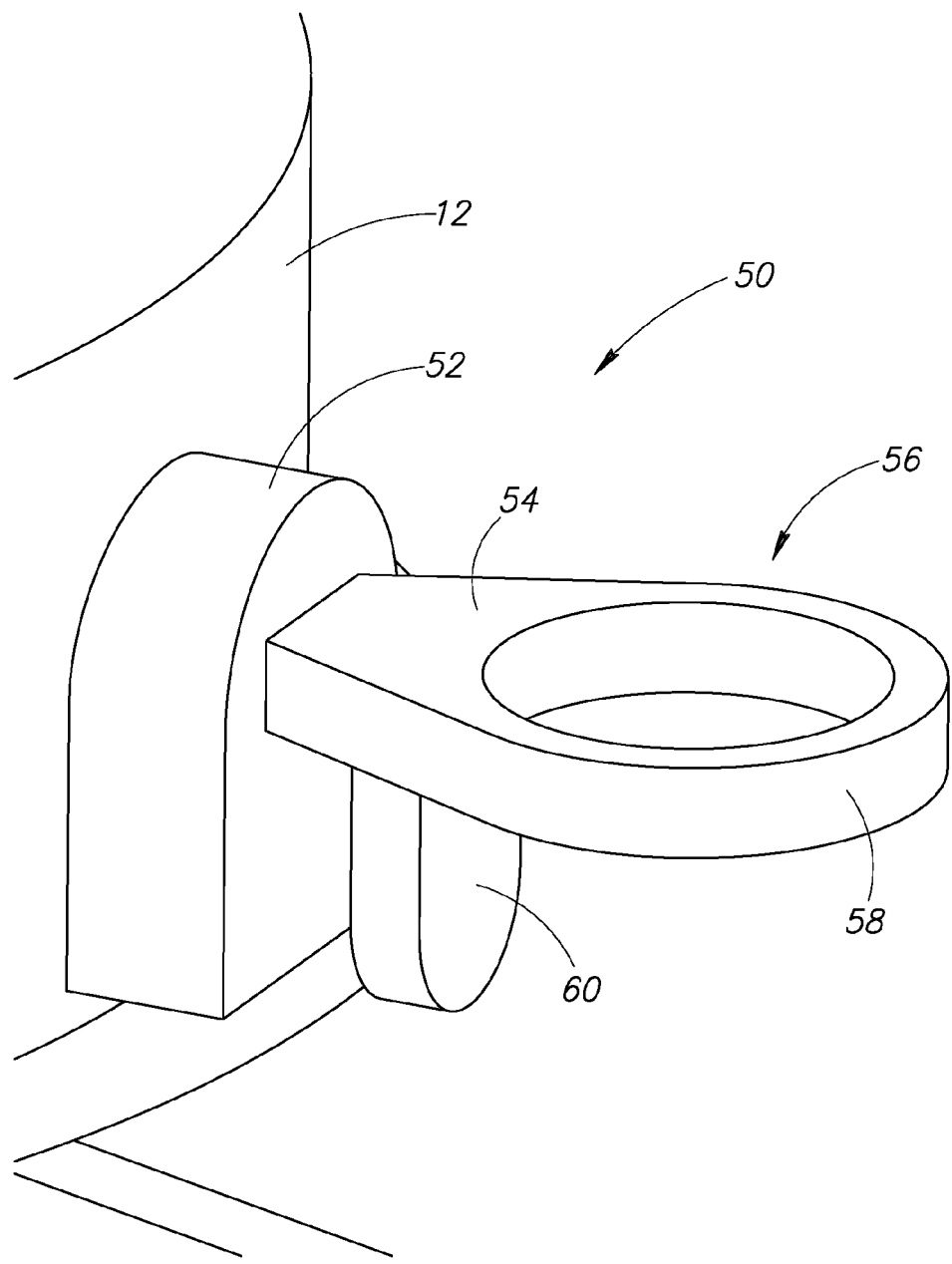
FIG. 2 is a perspective view of a tonometer holding assembly of the automatic tonometer tip disinfection apparatus according to an embodiment of the present invention.

FIG. 2 shows a close up of the tonometer holding assembly 50. The assembly preferably includes a base connector 52 affixed to or associated with a side of the rotating timer 12. The base connector 52 includes a shaft 54 that protrudes substantially perpendicular to the base connector away from the rotating timer and movably connects to a support arm assembly 56, preferably having a ring 58, configured to support the tonometer tip 70 (shown in FIG. 1) and a counterweight 60 that preferably extends away from the ring and provides a default orientation of the ring assembly during operation. The movable connection between the shaft 54 and support arm assembly 56 allows the assembly to freely rotate around the shaft. In an different embodiment, a support arm assembly 56 other than a ring may include a movable or grabbing robotic arm, hook, basket or other securing device that allows for movement of the tonometer tip into and out of each basin either by pivotal or vertical movement as the support arm assembly moves with respect to each of the basins.

The preferred operation of the invention is described with reference to FIGS. 1 and 2. The first basin 20 is filled with a disinfecting solution, for example, peroxide, preferably to the fluid level mark 28. The second basin 30 is filled with a rinsing solution, for example, water, preferably to the fluid level mark 38. The rotating timer 12 is rotated until the base connector 52 of the tonometer holding assembly 50 contacts the bumper 42, thus preventing further rotation. At this point the tonometer holding assembly 50 is positioned substantially at the front wall 22 of the first basin 20.

The tonometer tip 70 is secured in the ring 58 of the support arm assembly 56, preferably held in place by friction between the tonometer tip 70 and the surface of the ring 58, wherein the counterweight 60 orients the tonometer tip 70 substantially vertical such that the tip end 72 sits at least partially in the disinfecting solution residing in the first basin 20. After the rotating timer is engaged, it slowly moves the tonometer holding assembly 50 and tip end 72 of the supported tonometer tip 70 through the disinfecting solution residing in the first basin 20 until counterweight 60 contacts the back wall 24 of the first basin 20, which causes the tonometer holding assembly 50 and supported tonometer tip 70 to pivot horizontally over the back wall 24. After the tonometer tip 70 and counterweight 60 clears the back wall 24 of the first basin 20 and the front wall 32 of the second basin 30 (which may be formed as a single wall), the counterweight 60 pivots the tonometer holding assembly 50 and supported tonometer tip 70 back to a substantially vertical orientation, with the tip end 72 now sitting at least partially in the rinsing solution residing in the second basin 30. The rotating timer continues to slowly move the tonometer holding assembly 50 and tip end 72 of the supported tonometer tip 70 through the rinsing solution residing in the second basin 30 until first the counterweight 60 then the ring 58 contacts the raised back wall 34 of the second basin 30, which pivots the tonometer holding assembly 50 and the supported tonometer tip 70 to a sufficient degree that the tonometer tip 70 is released from its friction fit within the ring 58 and drops onto the holding platform 40.

Figure 3:
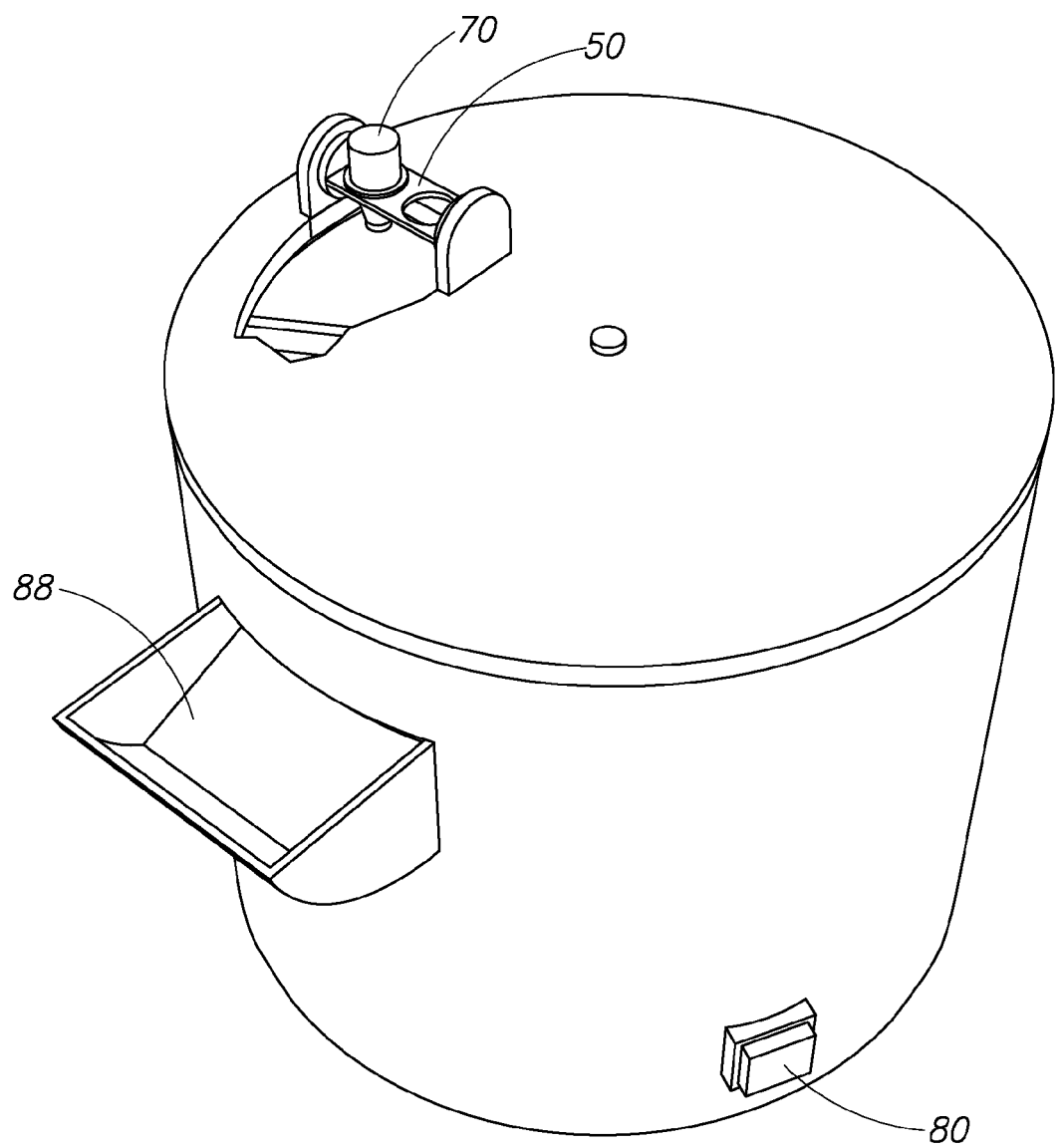
FIG. 3 is a perspective view of the automatic tonometer tip disinfection apparatus according to an embodiment of the present invention.
Figure 4:
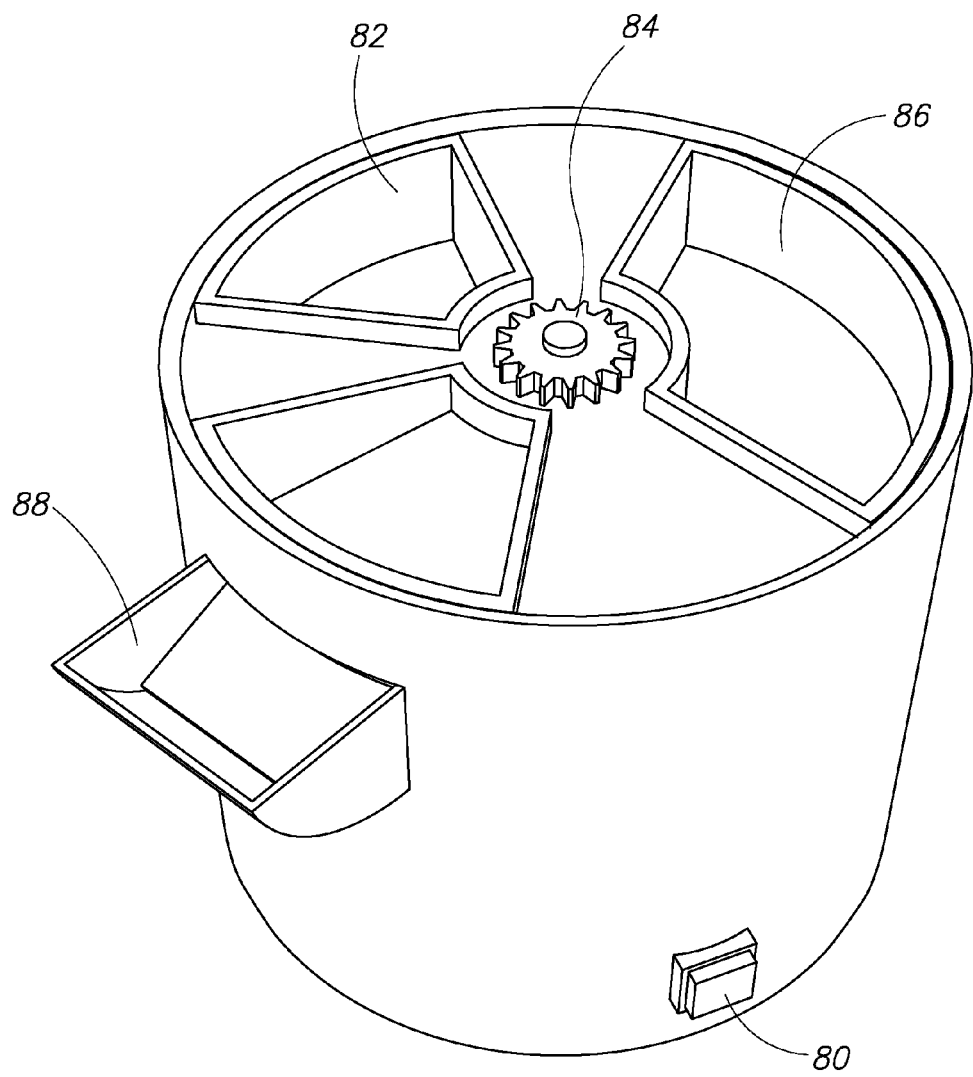
FIG. 4 is a partial cutaway view of the embodiment shown in FIG. 3.

An alternative embodiment is shown with reference to FIGS. 3 and 4. This embodiment incorporates an electronic timing circuit and power source (e.g., AC or battery) rather than a mechanical rotating timer. The timing circuit allows greater flexibility and user selectability for the period of time in which the tonometer tip 50 resides in the first and second basins 20,30 and, accordingly, the length of time required to complete the entire disinfection cycle. This alternative embodiment also provides for modification of the size of the basins required for the disinfecting staging areas as well as the overall size of the apparatus. In this embodiment, a switch 80 activates a timing circuit that allows one or more tonometer tips 70, residing in a tonometer holding assembly 50, to remain stationary positioned with the tip end 72 (not shown) residing in the disinfecting solution in a first basin 82 for a predetermined period of time. At the expiration of the predetermined period of time, a rotating motor gear 84 assembly well known in the art is activated, which rotates the tonometer tip 70 out of the first basin 82 into a second rinsing basin 86, where it may remain stationary for a predetermined period of time, after which it is ejected onto a holding platform 88.

Figure 5:
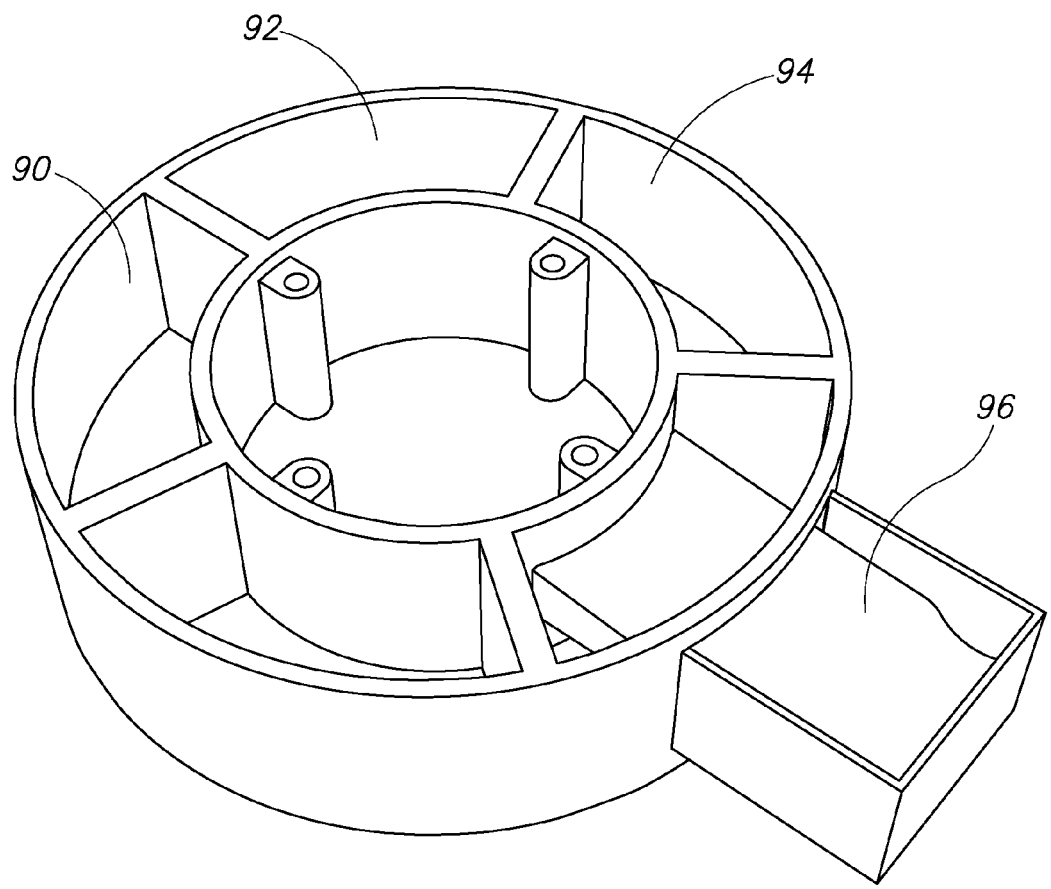
FIG. 5 is a partial cutaway view of the automatic tonometer tip disinfection apparatus according to an alternative embodiment of the present invention.

Yet another alternative embodiment is shown with reference to FIG. 5, further with reference to the elements of the invention described in FIGS. 1-4. This embodiment features a first basin 90 holding a disinfecting solution and second and third basins 92,94 holding a rinsing solution. Upon activation, the tonometer tip 50 is places in the disinfecting solution of the first basin 90 for a predetermined period of time, after which it is rotated sequentially to the rinsing solution in the second and third basins 92,94, after which the tonometer holding assembly 50 is rotated to a holding platform 96, where the tonometer tip 50 is released onto the platform to dry and be reused. This embodiment has the further advantage of ensuring that no disinfectant remains on the tonometer tip.

While the preferred embodiments of the invention has been illustrated and described, as noted above, many changes can be made without departing from the spirit and scope of the invention. By way of example, other embodiments may include the incorporation of multiple tonometer holding assemblies or a modified single tonometer assembly configured to hold a plurality of tonometer tips. A different number of disinfecting and rinsing basins may be used to facilitate varying degrees of disinfection and rinsing, or the application of different disinfecting or rinsing solutions in a plurality of basins into which the tonometer tips are placed. Multiple disinfecting and rinsing basins may separate or connected to simultaneous filing and refilling. Yet further alternative embodiments could include a rollercoaster type track as a mechanism to guide the tonometer tips in and out of the peroxide and water baths, or a combination of rollercoaster mechanism and pivoting mechanism could also be employed. Alternatively, rather than pivotable movement of the tonometer tip into each basin, vertical movement of the tonometer tip into and out of the solution in each basin as the transportation assemble moves from basin to basin may be used, for example, to allow the tonometer tip end to be lowered into each basin and raised for movement between basins. In yet alternative embodiments, the movement mechanism may push or pull the tonometer holding assembly(ies) through the disinfecting and rinsing solution basins rather than carrying them to each basin. Also, while the circular configuration described above provides for a compact apparatus footprint, another contemplated embodiment may include alternative configurations, for example, a linear track, wherein the tonometer holding assembly(ies) are moved from station to station to facilitate the placement of the tonometer tips in disinfecting and rinsing solutions. In this regard, the means for moving the tonometer holding assembly from station to station, or transportation assembly, may be anything configured to move the tonometer holding assembly between the one or more disinfecting basins and the one or more rinsing basins, for example, a mechanical rotating timer, an electronic timing circuit and rotating gear, a motorized track assembly that carries, pushes, or pulls the tonometer holding assembly, or the like. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. An apparatus for disinfecting and rinsing a tonometer tip, comprising:
   a support base;
   a first basin attached to the support base and configured to hold a disinfecting solution;
   at least one additional basin attached to the support base and configured to hold a rinsing solution;
   a tonometer tip support arm configured to support a tonometer tip having a tip end in an orientation allowing the tip end to reside at least in part within the first and at least one additional basins; and
   a transportation assembly configured to automatically move the tonometer tip support arm between the first and at least one additional basins and to move the tonometer tip circumferentially through the first and at least one additional basins;
   wherein the tonometer tip support arm comprises a pivoting member rotatably mounted to the transportation assembly and sized to receive the tonometer tip, the pivoting member having a protuberance secured thereto and positioned such that the protuberance engages a barrier between the first basin and the at least one additional basin causing the pivoting member and the tonometer tip to rotate above the barrier responsive to engagement of the protuberance with the barrier, the pivoting member further positioned such that the tonometer tip and pivoting member rotate responsive to gravity upon moving past the barrier during movement of the tonometer tip between the first basin and the at least one additional basin such that the tonometer tip is positioned within into the rinsing solution of the at least one additional basin.

2. The apparatus of claim 1, wherein the first and at least one additional basins are adjacent each other.

3. The apparatus of claim 1, wherein the first and at least one additional basins have fluid level marks indicating the preferred level of fluid to be supplied to each basin.

4. The apparatus of claim 3, wherein the fluid level mark for the at least one additional basin provides for a higher level of fluid in the at least one additional basin than the fluid level mark for the first basin.

5. The apparatus of claim 1, wherein the transportation assembly is configured to automatically move the tonometer tip support arm from the first basin to the at least one additional basin according to a predetermined time function.

6. The apparatus of claim 1, wherein
   the transportation assembly is a mechanical rotating timer that rotates according to a predetermined time function; and
   the mechanical rotating timer moves the tonometer tip support arm from the first basin to a second basin and to a holding platform according to the predetermined time function.

7. The apparatus of claim 1, wherein the transportation assembly is configured to move the tonometer tip over the barrier between the first basin and the at least one additional basin during movement of the tonometer tip between the first basin and the at least one additional basin and to move the tonometer tip into the rinsing solution of the at least one additional basin when the tonometer tip is positioned over the at least one additional basin during movement of the tonometer tip between the first basin and the at least one additional basin.

8. The apparatus of claim 7, wherein the tonometer tip support arm is configured for pivoting movement to allow the tip end to be lowered to reside at least in part within the first and at least one additional basin and pivot responsive to encountering one or more barriers between the first and at least one additional basin during transportation between basins.

9. The apparatus of claim 8, wherein the first and at least one additional basins are defined by an arcuate outer wall extending circumferentially around the transportation assembly and a barrier extending radially from the transportation assembly to the arcuate outer wall, the barrier separating the first basin from the at least one additional basin.

10. The apparatus of claim 9, wherein the tonometer tip support arm is configured for vertical movement to allow the tip end to be lowered to reside at least in part within the first basin and then within the at least one additional basin and raised for transportation between the first basin and the at least one additional basins.

\* \* \* \* \*

UNITED STATES PATENT AND TRADEMARK OFFICE
CERTIFICATE OF CORRECTION

PATENT NO. : 9,533,062 B2  
APPLICATION NO. : 14/550738  
DATED : January 3, 2017  
INVENTOR(S) : Andrew Peter Davis Page 1 of 1

It is certified that error appears in the above-identified patent and that said Letters Patent is hereby corrected as shown below:

In the Claims

In Column 5, Line 49 (Claim 1), remove "within".

Signed and Sealed this  
Fourth Day of April, 2017

Michelle K. Lee  
*Director of the United States Patent and Trademark Office*